United States Patent [19]

Zimmermann

[11] Patent Number: 5,521,184
[45] Date of Patent: May 28, 1996

[54] PYRIMIDINE DERIVATIVES AND PROCESSES FOR THE PREPARATION THEREOF

[75] Inventor: Jürg Zimmermann, Wallbach, Switzerland

[73] Assignee: Ciba-Geigy Corporation, Tarrytown, N.Y.

[21] Appl. No.: 234,889

[22] Filed: Apr. 28, 1994

Related U.S. Application Data

[63] Continuation-in-part of Ser. No. 42,322, Apr. 2, 1993, abandoned.

[30] Foreign Application Priority Data

| Apr. 3, 1992 | [CH] | Switzerland | 1083/92 |
| Oct. 1, 1993 | [CH] | Switzerland | 2966/93 |

[51] Int. Cl.⁶ .................... C07D 239/92; A61K 31/505
[52] U.S. Cl. .................... 514/252; 514/272; 544/295; 544/322; 544/331; 544/332
[58] Field of Search .................... 514/252, 272; 544/295, 322, 331, 332

[56] References Cited

U.S. PATENT DOCUMENTS

| 4,694,009 | 9/1987 | Hubele et al. | 514/269 |
| 4,788,195 | 11/1988 | Torley et al. | 514/252 |
| 4,876,252 | 10/1989 | Torley et al. | 514/224.8 |
| 4,940,712 | 7/1990 | Walker et al. | 514/272 |

FOREIGN PATENT DOCUMENTS

| 2093203 | 10/1993 | Canada . |
| 564409A1 | 4/1982 | European Pat. Off. . |
| 0168262 | 1/1985 | European Pat. Off. . |
| 0164204 | 12/1985 | European Pat. Off. . |
| 0233461 | 8/1987 | European Pat. Off. . |
| 337943A | 10/1989 | European Pat. Off. . |
| 388838A | 9/1990 | European Pat. Off. . |
| 0453731 | 10/1991 | European Pat. Off. . |
| 3436380A | 4/1986 | Germany . |

OTHER PUBLICATIONS

90–231199/30 Derwent Abstract (1990) 1990 Corresponding to U.S. Pat. No. 4,940,712—Pfizer Inc.
89–167195 Derwent Abstract (1989) corresponding to EP 319,170—Pfizer Inc.

*Primary Examiner*—Mukund J. Shah
*Assistant Examiner*—Matthew V. Grumbling
*Attorney, Agent, or Firm*—Karen G. Kaiser

[57] ABSTRACT

There are described N-phenyl-2-pyrimidine-amine derivatives of formula I

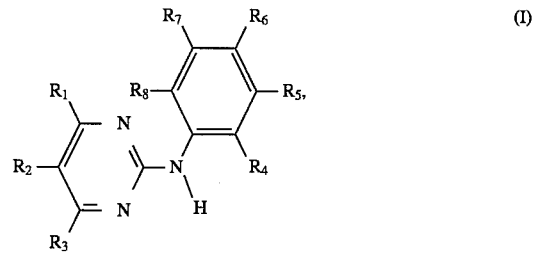

wherein $R_1$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, $R^2$, $R^3$, $R^9$, X, Y, n and $R^{10}$ are defined in claim 1

These compounds can be used, for example, in the therapy of tumoral diseases.

23 Claims, No Drawings

PYRIMIDINE DERIVATIVES AND PROCESSES FOR THE PREPARATION THEREOF

This is a continuation-in-part application of U.S. patent application Ser. No. 08/042,322, filed Apr. 2, 1993, now abandoned.

The invention relates to N-phenyl-2-pyrimidine-amine derivatives, to processes for the preparation thereof, to medicaments comprising those compounds, and to the use thereof in the preparation of pharmaceutical compositions for the therapeutic treatment of warm-blooded animals.

The invention relates to N-phenyl-2-pyrimidine-amine derivatives of formula I

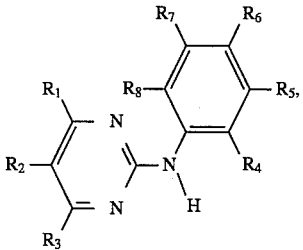

wherein $R_1$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one or two of the radicals $R_4$, $R_5$, $R_6$, $R_7$ and $R_8$ are each nitro, fluoro-substituted lower alkoxy or a radical of formula II

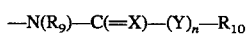

wherein $R_9$ is hydrogen or lower alkyl,

X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, and to salts of such compounds having at least one salt-forming group.

1-Methyl-1H-pyrrolyl is preferably 1-methyl-1H-pyrrol-2-yl or 1-methyl-1H-pyrrol-3-yl.

Amino- or amino-lower alkyl-substituted phenyl $R_1$ wherein the amino group in each case is free, alkylated or acylated is phenyl substituted in any desired position (ortho, meta or para) wherein an alkylated amino group is preferably mono- or di-lower alkylamino, for example dimethylamino, and the lower alkyl moiety of amino-lower alkyl is preferably linear $C_1$–$C_3$alkyl, such as especially methyl or ethyl.

1H-Indolyl bonded at a carbon atom of the five-membered ring is 1H-indol-2-yl or 1H-indol-3-yl.

Unsubstituted or lower alkyl-substituted pyridyl bonded at a ring carbon atom is lower alkyl-substituted or preferably unsubstituted 2-, or preferably 3- or 4-pyridyl, for example 3-pyridyl, 2-methyl-3-pyridyl, 4-methyl-3-pyridyl or 4-pyridyl. Pyridyl substituted at the nitrogen atom by oxygen is a radical derived from pyridine N-oxide, i.e. N-oxido-pyridyl, e.g. N-oxido-4-pyridyl.

Fluoro-substituted lower alkoxy is lower alkoxy carrying at least one, but preferably several, fluoro substituents, especially trifluoromethoxy or preferably 1,1,2,2-tetrafluoro-ethoxy.

When X is oxo, thio, imino, N-lower alkyl-imino, hydroximino or O-lower alkyl-hydroximino, the group C=X is, in the above order, a radical C=O, C=S, C=N—H, C=N-lower alkyl, C=N—OH or C=N—O-lower alkyl, respectively. X is preferably oxo.

n is preferably 0, i.e. the group Y is not present.

Y, if present, is preferably the group NH.

The term "lower" within the scope of this text denotes radicals having up to and including 7, preferably up to and including 4 carbon atoms.

Lower alkyl $R_1$, $R_2$, $R_3$ and $R_9$ is preferably methyl or ethyl.

An aliphatic radical $R_{10}$ having at least 5 carbon atoms preferably has not more than 22 carbon atoms, generally not more than 10 carbon atoms, and is such a substituted or preferably unsubstituted aliphatic hydrocarbon radical, that is to say such a substituted or preferably unsubstituted alkynyl, alkenyl or preferably alkyl radical, such as $C_5$–$C_7$alkyl, for example n-pentyl. An aromatic radical $R_{10}$ has up to 20 carbon atoms and is unsubstituted or substituted, for example in each case unsubstituted or substituted naphthyl, such as especially 2-naphthyl, or preferably phenyl, the substituents preferably being selected from cyano, unsubstituted or hydroxy-, amino- or 4-methyl-piperazinyl-substituted lower alkyl, such as especially methyl, trifluoromethyl, free, etherified or esterified hydroxy, free, alkylated or acylated amino and free or esterified carboxy. In an aromatic-aliphatic radical $R_{10}$ the aromatic moiety is as defined above and the aliphatic moiety is preferably lower alkyl, such as especially $C_1$–$C_2$alkyl, which is substituted or preferably unsubstituted, for example benzyl. A cycloaliphatic radical $R_{10}$ has especially up to 30, more especially up to 20, and most especially up to 10 carbon atoms, is mono- or poly-cyclic and is substituted or preferably unsubstituted, for example such a cycloalkyl radical, especially such a 5- or 6-membered cycloalkyl radical, such as preferably cyclohexyl. In a cycloaliphatic-aliphatic radical $R_{10}$ the cycloaliphatic moiety is as defined above and the aliphatic moiety is preferably lower alkyl, such as especially $C_1$–$C_2$alkyl, which is substituted or preferably unsubstituted. A heterocyclic radical $R_{10}$ contains especially up to 20 carbon atoms and is preferably a saturated or unsaturated monocyclic radical having 5 or 6 ring members and 1-3 hetero atoms which are preferably selected from nitrogen, oxygen and sulfur, especially, for example, thienyl or 2-, 3- or 4-pyridyl, or a bi- or tri-cyclic radical wherein, for example, one or two benzene radicals are annellated (fused) to the mentioned monocyclic radical. In a heterocyclic-aliphatic radical $R_{10}$ the heterocyclic moiety is as defined above and the aliphatic moiety is preferably lower alkyl, such as especially $C_1$–$C_2$alkyl, which is substituted or preferably unsubstituted.

Etherified hydroxy is preferably lower alkoxy. Esterified hydroxy is preferably hydroxy esterified by an organic carboxylic acid, such as a lower alkanoic acid, or a mineral acid, such as a hydrohalic acid, for example lower alkanoyloxy or especially halogen, such as iodine, bromine or especially fluorine or chlorine.

Alkylated amino is, for example, lower alkylamino, such as methylamino, or di-lower alkylamino, such as dimethylamino. Acylated amino is, for example, lower alkanoylamino or benzoylamino.

Esterified carboxy is, for example, lower alkoxycarbonyl, such as methoxycarbonyl.

A substituted phenyl radical may carry up to 5 substituents, such as fluorine, but especially in the case of relatively large substituents is generally substituted by only from 1 to 3 substituents. Examples of substituted phenyl that may be given special mention are 4-chloro-phenyl, pentafluorophenyl, 2-carboxy-phenyl, 2-methoxy-phenyl, 4-fluorophenyl, 4-cyano-phenyl and 4-methyl-phenyl.

Salt-forming groups in a compound of formula I are groups or radicals having basic or acidic properties. Compounds having at least one basic group or at least one basic radical, for example a free amino group, a pyrazinyl radical or a pyridyl radical, may form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

Compounds of formula I having acidic groups, for example a free carboxy group in the radical $R_{10}$, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethylpiperidine or N,N'-dimethyl-piperazine.

Compounds of formula I having both acidic and basic groups can form internal salts.

For the purposes of isolation or purification, as well as in the case of compounds that are used further as intermediates, it is also possible to use pharmaceutically unacceptable salts. Only pharmaceutically acceptable, non-toxic salts are used for therapeutic purposes, however, and those salts are therefore preferred.

Owing to the close relationship between the novel compounds in free form and in the form of their salts, including those salts that can be used as intermediates, for example in the purification of the novel compounds or for the identification thereof, hereinbefore and hereinafter any reference to the free compounds should be understood as including the corresponding salts, where appropriate and expedient.

The compounds of formula I have valuable pharmacological properties and can be used, for example, as antitumoral drugs and as drags against atherosclerosis.

The phosphorylation of proteins has long been known as an important step in the differentiation and proliferation of cells. The phosphorylation is catalysed by protein kinases which are divided into serine/threonine kinases and tyrosine kinases. The serine/threonine kinases include protein kinase C and the tyrosine kinases the PDGF (platelet-derived growth factor)-receptor tyrosine kinase.

The compounds of formula I wherein $R_4$ and $R_8$ are hydrogen selectively inhibit the enzyme protein kinase C.

Several species of protein kinase C, which is dependent on phospholipids and calcium, occur within cells (distribution of the species is tissue-specific); protein kinase C participates in various fundamental processes, such as signal transmission, proliferation and differentiation, as well as the release of hormones and neurotransmitters. The enzyme is activated either by means of receptor-mediated hydrolysis of phospholipids of the cell membrane or by direct interaction with certain tumour-promoting agents. Cellular functions that are controlled with the aid of protein kinase C can be influenced by modulation of the enzyme activity of protein kinase C.

To determine protein kinase C-inhibiting activity, protein kinase C from pig brain purified in accordance with the procedure described by T. Uchida and C. R. Filburn in J. Biol. Chem. 259, 12311–4 (1984) is used. The protein kinase C-inhibiting activity of the compounds of formula I is determined by the method of D. Fabbro et at., Arch. Biochem. Biophys. 239, 102–111 (1985). In that test the compounds of formula I inhibit protein kinase C at a concentration $IC_{50}$ of as low as approximately from 0.1 to 10 μmol/liter, especially approximately from 0.05 to 5 μmol/liter. On the other hand, the compounds of formula I inhibit other enzymes, for example protein kinase A, phosphorylase protein kinase and certain types of tyrosine protein kinase, for example the tyrosine protein kinase of EGF (epidermal growth factor) receptors, only at a far higher concentration, for example 100 times higher. That is an indication of the selectivity of the compounds of formula I. With a view to reducing undesired side effects, it is important for the protein kinase C-inhibitors to be as selective as possible, i.e. inter alia to have as little effect as possible on other enzymes, especially when the effect of the activity of those other enzymes has no equivalent or synergistic effect on the disease to be treated.

The protein kinase C from pig brain mentioned above is a mixture of different subtypes (isotypes) of protein kinase C. If pure recombinant isotypes are used in the above assay instead of protein kinase C from pig brain, it is found that the compounds of formula I inhibit preferably the other "conventional" α-isotypes, whereas the other "conventional" β-1-, β2- and γ-isotypes, as well as in particular the "non-conventional" δ-, ε- and η-isotypes and the "atypical" ζ-isoform, are inhibited to a lesser degree or are virtually not inhibited at all.

Recombinant PKC isotypes are cloned, expressed and purified as follows:

The preparation of different proteins using baculoviruses and their cloning and isolation from Sf9 insect cells is carded out as described by M. D. Summers and G. E. Smith, "A manual method for baculovirus vectors and insect cell culture procedure", Texas Agricul. Exptl. Station Bull. (1987), 1555. The construction and isolation of recombinant viruses for the expression of PKC-α (beef), PKC-β1 (human), PKC-β2 (human) as well as PKC-γ (human/beef hybrid) in Sf9 cells is carded out as described by Stabel et al. [S. Stabel, M. Liyanage and D. Frith, "Expression of protein kinase C isozymes in insect cells and isolation of recombinant proteins", Meth. Neurosc. (1993)]. The preparation of the PKC isotypes in Sf9 cells is carded out as described by Stabel et al. (q.v. above), and the purification of the enzymes is carded out by the method described in the publication of McGlynn et at. [E. McGlynn, J. Liebetanz, S. Reutener, J. Wood, N. B. Lydon, H. Hofstetter, M. Vanek, T. Meyer and D. Fabbro, "Expression and partial characterization of rat protein kinase C-δ and protein kinase C-ζ in insect cells using recombinant baculovirus", J. Cell. Biochem. 49, 239–250 (1992)]. The generation of recombinant PKC-δ (rats), PKC-ε (rats), PKC-δ (rats) ad PKC-η (mice), and their expression and purification, is carried out in accordance with the procedure described by Liyanage et.al. ["Protein kinase C group B members PKC-δ, -ε, -ζ and PKC-λ: Comparison of properties of recombinant proteins in vitro and in vivo", Biochem. J. 283, 781–787 (1992)] and McGlynn et. al. (q.v. above), using additionally for the expression of PKC-η the transfer vector pAc360 [V. Luckow and M. D. Summers, "Trends in the development of baculovirus expression", Biotechnology 6, 47–55 (1988)].

The measurement of the activity of the recombinant PKC isotypes obtained by the above method is carded out in the absence of lipid and calcium (co-factors). This is done by using protamine sulfate, which is phosphorylated in the absence of co-factors, as substrate. The activity of the enzymes reflects the transfer of $^{32}P$ from $\gamma$-$[^{32}P]$-ATP to protamine sulfate. Protamine sulfate is a mixture of polypeptides, each containing four C-terminal arginine radicals. The measurement of the phosphate incorporation is carded out under the following conditions: 100 μl of the reaction mixture contain in final concentrations 20 mM of TRIS-HCl pH 7.4, 10 mM of $Mg[NO_3]_2$, 0.5 mg/ml of protamine sulfate, 10 μM of ATP (0.1 μCi $\gamma$-$[^{32}P]$-ATP; 10 Ci/mol; Amersham, Little Chalfont, United Kingdom), different concentrations of the inhibitory substances and 0.5–2.5 U (units; one unit is the amount of enzyme which, in one minute per milligram of protein, transfers one nanomol $^{32}P$ of the above mentioned $\gamma$-$[^{32}P]$-ATP to histone H1 [sigma, type V-S]) of the enzymes. The reaction is initiated by addition of the enzymes and transfer to 32° C. The reaction time is 20 minutes. Afterwards the reaction is halted by the dropwise addition of aliquots of 50 μl on to P81 chromatography paper (Whatman, Maidstone, United Kingdom). After removal of unbound $\gamma$-$[^{32}P]$-ATP and fraction nucleotides by washing procedures as described by J. J. Witt and R. Roskoski, "Rapid protein kinase assay using phosphocellulose-paper absorption", Anal. Biochem. 66, 253–258 (1975), the substrate phosphorylation is determined by scintillation measurement. In this assay, the compounds of formula I inhibit the α-isotypes of protein kinase C (PKC) at an $IC_{50}$ concentration of about 0.1 to 5.0 μmol/liter, usually of about 0.1 to 1.0 μmol/liter. The other isotypes of PKC are by comparison usually inhibited only at markedly higher (i.e. up to more than 300-fold) concentrations.

Owing to their inhibiting activity towards protein kinase C, the compounds of formula I wherein $R_4$ and $R_8$ are hydrogen, and their pharmaceutically acceptable salts, can be used as tumour-inhibiting, immunomodulating and antibacterial active ingredients and, further, as drugs against atherosclerosis, the immunodeficiency disorder AIDS, and diseases of the cardiovascular system and the central nervous system.

As might already be expected on the basis of the inhibiting action on protein kinase C described above, the compounds of formula I wherein $R_4$ and $R_8$ are hydrogen, and their pharmaceutically acceptable salts, have anti-proliferative properties which can be demonstrated directly in the following, different test. In that test the inhibiting action of compounds of formula I on the growth of human T24 bladder carcinoma cells is determined. Those cells are incubated in "Eagle's minimal essential medium", to which 5% (v/v) foetal calf serum has been added, in a humidified incubator at 37° C. and with 5 percent by volume $CO_2$ in the air. The carcinoma cells (1000–1500) are transferred to 96-well microtitre plates and incubated overnight under the above-mentioned conditions. The test compound is added in serial dilutions on day 1. The plates are incubated for 5 days under the above-mentioned conditions. During that period the control cultures undergo at least 4 cell divisions. After the incubation, the cells are fixed with 3.3% (g/v) aqueous glutaraldehyde solution, washed with water and stained with 0.05% (weight/volume) aqueous methylene blue solution. After washing, the stain is eluted with 3% (g/v) aqueous hydrochloric acid. Then the optical density (OD) per well, which is directly proportional to the number of cells, is measured using a photometer (Titertek multiskan) at 665 nm. The $IC_{50}$ values are calculated by means of a computer system, using the formula $$\frac{OD_{665} \text{ (test) minus } OD_{665} \text{ (start)}}{OD_{665} \text{ (control) minus } OD_{665} \text{ (start)}} \times 100$$

The $IC_{50}$ values are defined as that concentration of active ingredient at which the number of cells per well at the end of the incubation period is only 50% of the number of cells in the control cultures. The $IC_{50}$ values thus determined are, for the compounds of formula I, approximately from 0.1 to 10 μmol/liter.

The tumour-inhibiting activity of the compounds of formula I can also be demonstrated in vivo.

The tumour-inhibiting activity is determined using female Balb/c nude mice in which human T24 bladder carcinoma has been transplanted. On day 0, a c. 25 mg piece of solid tumour is transplanted subcutaneously under peroral "forene" narcosis on the left flank and the small incision wound is closed with a suture clip. On day 6 after the tumour transplantation, the mice are randomised in groups of 6 animals and treatment is commenced. The treatment is carded out for 15 days by administering a compound of formula I, e.g. N-[3-(1,1,2,2-Tetrafluoroethoxy)phenyl]-4-(4-pyridyl)-2-pyrimidine-amine, in dimethyl sulfoxide/Tween 80/sodium chloride solution in the different doses perorally or intraperitoneally once daily. The tumours are measured twice weekly with a sliding caliper and the tumour volume determined. In this assay, the peroral or intraperitoneal administration of a compound of formula I effects a marked reduction in the average tumour volume compared with the untreated controls.

Owing to the properties described, the compounds of formula I wherein $R_4$ and $R_8$ are hydrogen can be used especially as tumour-inhibiting active ingredients, for example for the treatment of tumours of the bladder. In addition, they are suitable for the further applications mentioned above for protein kinase C-modulators and can be used especially in the treatment of diseases that respond to inhibition of protein kinase C.

Some of the compounds of formula I wherein $R_4$ and $R_8$ are hydrogen inhibit not only protein kinase C but, at a concentration $IC_{50}$ as low as approximately from 0.01 to 5 μmol/liter, especially approximately from 0.05 to 1 μmol/liter, also certain tyrosine kinases, such as especially PDGF-receptor kinase or abl-kinase, for example v-abl-kinase.

Compounds of formula I wherein at least one of the radicals $R_4$ and $R_8$ is other than hydrogen and is, for example, lower alkyl, such as methyl, are especially selective for the above-mentioned PDGF-receptor and abl-tyrosine kinases and inhibit protein kinase C virtually not at all.

PDGF (platelet-derived growth factor) is a very frequently occurring growth factor which plays an important role both in normal growth and in pathological cell proliferation, such as in carcinogenesis and disorders of the smooth muscle cells of blood vessels, for example in atherosclerosis and thrombosis.

The inhibition of protein kinase C and of PDGF-receptor kinase has in this sense a virtually synergistic effect in the same direction with regard to the regulation of cell growth.

The inhibition of PDGF-stimulated receptor tyrosine kinase activity in vitro is measured in PDGF receptor immunocomplexes of BALB/c 3T3 cells, analogously to the method described by E. Andrejauskas-Buchdunger and U. Regenass in Cancer Research 52, 5353–5358 (1992). The compounds of formula I described in detail above inhibit PDGF-dependent cell-free receptor phosphorylation at concentrations of from 0.005 to 5 µmol/liter, especially from 0.01 to 1.0, more especially from 0.01 to 0.1 µmol/liter. The inhibition of PDGF-receptor tyrosine kinase in the intact cell is detected by means of Western Blot Analysis, likewise analogously to the method described by E. Andrejauskas-Buchdunger and U. Regenass in Cancer Research 52, 5353–5358 (1992). In that test the inhibition of ligand-stimulated PDGF-receptor autophosphorylation in BALB/c mouse cells is measured with the aid of anti-phosphotyrosine antibodies. The compounds of formula I described in detail above inhibit the tyrosine kinase activity of the PDGF receptor at concentrations of from 0.005 to 5 µmol/liter, especially from 0.01 to 1.0 and more especially from 0.01 to 0.1 µmol/liter. At concentrations below 1.0 µmol/liter, those compounds also inhibit the cell growth of a PDGF-dependent cell line, namely BALB/c 3T3 mouse fibroblasts.

The above-mentioned inhibition of v-abl-tyrosine kinase is determined in accordance with the methods of N. Lydon et at., Oncogene Research 5, 161–173 (1990) and J. F. Geissler et al., Cancer Research 52, 4492–4498 (1992). In those methods [Val$^5$]-angiotensin II and [γ-$^{32}$P]-ATP are used as substrates.

Owing to the properties described, compounds of formula I can be used not only as tumour-inhibiting active ingredients but also as drugs against non-malignant proliferative diseases, e.g. atherosclerosis, thrombosis, psoriasis, sclerodermitis and fibrosis. They are also suitable for the further applications mentioned above for protein kinase C-modulators and can be used especially in the treatment of diseases that respond to the inhibition of PDGF-receptor kinase.

Some of the compounds of formula I, e.g. N-[3-(1,1,2,2-tetrafluoroethoxy)phenyl]-4-(3-indolyl)-2-pyrimidine-amine, furthermore inhibit the tyrosine kinase activity of the receptor for the epidermal growth factor (EGF). This receptor-specific enzyme activity is a key factor in the signal transmission in a host of mammalian cells, including human cells, especially epithelial cells, cells of the immune system and cells of the central and peripheral nervous system. The EGF-induced activation of the receptor-associated protein tyrosine kinase (EGF-R-PTK) is in many cells a prerequisite for cell division and hence for the proliferation of a cell population. The addition of EGF-receptor-specific tyrosine kinase inhibitors thus inhibits the replication of these cells.

The inhibition of the EGF-receptor-specific protein tyrosine kinase (EGF-R-PTK) can be demonstrated, inter alia, by the method of E. McGlynn et at., Europ. J. Biochem. 207, 265–275 (1992). The compounds of this invention inhibit enzyme activity by 50% (IC$_{50}$) typically in a concentration of 0.1 to 10 µm.

These compounds of formula I, which inhibit the tyrosine kinase activity of the receptor for the epidermal growth factor (EGF) are therefore useful, inter alia, for the treatment of benign or malignant tumours. They are able to effect tumour regression and to prevent metastasic spread and the growth of micrometastases. In particular, they can be used for treating epidermal hyperproliferation (psoriasis), for treating neoplasms of epithelial character, e.g. mastocarcinomas, and leucemias. In addition, the compounds of formula I are useful for treating diseases of the immune system and inflammations, subject to the involvement of protein kinases. These compounds of formula I can also be used for treating diseases of the central or peripheral nervous system, subject to the involvement of signal transmission by protein kinases.

Some of the compounds of the formula I, e.g. N-[3-(1,1,2,2-tetrafluoroethoxy)phenyl]-4-(4-pyridyl)-2-pyrimidine-amine, also inhibit the enzyme p34$^{cdc2}$/cyclin B$^{cdc13}$ kinase. Among other cdc2-related kinases, said kinase regulates certain phases of the cell division, especially the transition of the G$_1$ phase into the S phase and above all the transition of the G$_2$ phase into the M phase.

The cycle of an eukaryotic cell consists in chronological order of the interphase and the M phase. During the interphase the cell grows in size. The interphase itself consists in chronological order of the G$_1$ phase, the S-phase, and the G$_2$ phase. In the G$_1$ phase (G=gap) biosynthetic processes are going on in the cell. During the S phase (S=synthesis) the DNA is replicated. Thereafter the cell enters the G$_2$ phase which ends with the beginning of mitosis.

The M phase itself consists in chronological order of the division of the nucleus (mitosis) and the division of the cytoplasma (cytokinesis).

The above-mentioned inhibition of the enzyme p34$^{cdc2}$/cyclin B$^{cdc13}$ kinase can be demonstrated by the following test:

Starfish oocytes are induced to enter M phase with 10 µM 1-methyladenine, frozen in liquid nitrogen and stored at −80° C. When required the oocytes are homogenized and centrifuged as described by D. Arion et al., Cell 55, 371–378 (1988) and V. Rialet und L. Meijer, Anticancer Res. 11, 1581–1590 (1991). For purification of p34$^{cdc2}$/cyclin B$^{cdc13}$ kinase, the supernatant of oocytes is added to p9$^{CKShs}$-sepharose beads prepared from recombinant human p9$^{CKShs}$ as described by L. Azzi et al., Eur. J. Biochem. 203, 353–360 (1992). After 30 minutes at 4° C. under constant rotation, the beads are extensively washed and active p34$^{cdc2}$/cyclin B$^{cdc13}$ kinase is eluted with free p9$^{CKShs}$ (3 mg/ml). The eluted kinase is assayed using histone H1 as a substrate as described by L. Meijer et al., EMBO J. 8, 2275–2282 (1989) und EMBO J. 10, 1545–1554 (1991). The reaction mixture contains 10 µl p34$^{cdc2}$/cyclin B$^{cdc13}$ kinase, 5 µl histone H1, type III-S (5 mg/ml) and 10 µl buffer C. The reaction is started by addition of 5 µl [γ-$^{32}$P]ATP (75 µM, 8800 cpm/pmole) and incubated for 10 minutes at 30° C. The assay is terminated by transferring 25 µl on pieces of Whatman P81 phosphocellulose paper. After 20 seconds the papers are washed 6 times with each 10 ml of 1% phosphoric acid for 5 minutes, dried and counted in a scintillation counter.

In the above-described test, compounds of the formula I, like N-[3-(1,1,2,2-tetrafluoroethoxy)phenyl]-4-(4-pyridyl)-2-pyrimidine-amine, exhibit IC$_{50}$ values from about 0.01 to 1 µmol/liter, e.g. 0.08 µmol/liter.

In addition, the compounds of formula I prevent the development of resistance (multi-drug resistance) in cancer treatment with other chemotherapeutic drugs or remove existing resistance to other chemotherapeutic drugs.

Of particular interest, inter alia as starting materials for the manufacture of other compounds of the formula I, are compounds of the formula I wherein one or two of the radicals $R_4$, $R_5$, $R_6$, $R_7$ and $R_8$, especially $R_7$, are each nitro, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, and the salts of such compounds having at least one salt-forming group.

Of particular interest are also compounds of the formula I wherein one or two of the radicals $R_4$, $R_5$, $R_6$, $R_7$ and $R_8$, especially $R_7$, represent fluoro-substituted lower alkoxy, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, or a salt of such a compound having at least one salt-forming group.

Preference is given to compounds of formula I wherein one or two of the radicals $R_4$, $R_5$, $R_6$, $R_7$ and $R_8$ are each nitro or a radical of formula II wherein $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy, and the remaining substituents are as defined above, and to salts of such compounds having at least one salt-forming group.

Preference is given especially to compounds of formula I wherein $R_1$ is 4-pyrazinyl, 1-methyl-1H-pyrrolyl, amino- or amino-lower alkyl-substituted phenyl wherein the amino group in each case is free, alkylated by one or two lower alkyl radicals or acylated by lower alkanoyl or by benzoyl, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one or two of the radicals $R_4$, $R_5$, $R_6$, $R_7$ and $R_8$ are each nitro, fluoro-substituted lower alkoxy or a radical of formula II wherein $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic hydrocarbon radical having 5–22 carbon atoms, a phenyl or naphthyl radical each of which is unsubstituted or substituted by cyano, lower alkyl, hydroxy-lower alkyl, amino-lower alkyl, (4-methyl-piperazinyl)-lower alkyl, trifluoromethyl, hydroxy, lower alkoxy, lower alkanoyloxy, halogen, amino, lower alkylamino, di-lower alkylamino, lower alkanoylamino, benzoylamino, carboxy or by lower alkoxycarbonyl, or phenyl-lower alkyl wherein the phenyl radical is unsubstituted or substituted as indicated above, a cycloalkyl or cycloalkenyl radical having up to 30 carbon atoms, cycloalkyl-lower alkyl or cycloalkenyl-lower alkyl each having up to 30 carbon atoms in the cycloalkyl or cycloalkenyl moiety, a monocyclic radical having 5 or 6 ring members and 1–3 ring hetero atoms selected from nitrogen, oxygen and sulfur, to which radical one or two benzene radicals may be fused, or lower alkyl substituted by such a monocyclic radical, and the remaining radicals $R_4$, $R_5$, $R_6$, $R_7$ and $R_8$ are each independently of the others hydrogen, lower alkyl that is unsubstituted or substituted by amino, lower alkylamino, di-lower alkylamino, piperazinyl, piperidinyl, pyrrolidinyl or by morpholinyl, or lower alkanoyl, trifluoromethyl, hydroxy, lower alkoxy, lower alkanoyloxy, halogen, amino, lower alkylamino, di-lower alkylamino, lower alkanoylamino, benzoylamino, carboxy or lower alkoxycarbonyl, and to salts of such compounds having at least one salt-forming group.

Special preference is given to compounds of formula I wherein $R_1$ is pyridyl bonded at a ring carbon atom and unsubstituted or substituted at the nitrogen atom by oxygen, $R_2$ and $R_3$ are each hydrogen, $R_4$ is hydrogen or lower alkyl, $R_5$ is hydrogen, lower alkyl or fluoro-substituted lower alkoxy, $R_6$ is hydrogen, $R_7$ is nitro, fluoro-substituted lower alkoxy or a radical of formula II wherein $R_9$ is hydrogen, X is oxo, n is 0 and $R_{10}$ is an aliphatic hydrocarbon radical having 5–22 carbon atoms, a phenyl radical that is unsubstituted or substituted by cyano, lower alkyl, (4-methyl-piperazinyl)-lower alkyl, lower alkoxy, halogen or by carboxy; a cycloalkyl radical having up to 30 carbon atoms or a monocyclic radical having 5 or 6 ring members and 1–3 sulfur ring atoms, and $R_8$ is hydrogen, and to pharmaceutically acceptable salts of such compounds having at least one salt-forming group.

Special preference is given especially to compounds of formula I wherein $R_1$ is pyridyl or N-oxido-pyridyl each of which is bonded at a carbon atom, $R_2$ and $R_3$ are each hydrogen, $R_4$ is hydrogen or lower alkyl, $R_5$ is hydrogen, lower alkyl or trifluoromethyl, $R_6$ is hydrogen, $R_7$ is nitro, fluoro-substituted lower alkoxy or a radical of formula II wherein $R_9$ is hydrogen, X is oxo, n is the number 0 and $R_{10}$ is pyridyl bonded at a carbon atom, phenyl that is unsubstituted or substituted by halogen, cyano, lower alkoxy, carboxy, lower alkyl or by 4-methyl-piperazinyl-methyl, or $C_5$–$C_7$alkyl, thienyl, 2-naphthyl or cyclohexyl, and $R_8$ is hydrogen, and to pharmaceutically acceptable salts of such compounds having at least one salt-forming group.

Preference is given above all to compounds of formula I wherein $R_4$ and $R_8$ are each hydrogen or wherein at least one of the radicals $R_4$ and $R_8$ is lower alkyl, and the other of the radicals $R_4$ and $R_8$ and the remaining radicals are as defined above, and to pharmaceutically acceptable salts of such compounds having at least one salt-forming group.

Preference is given above all especially to compounds of formula I wherein $R_1$ is pyridyl bonded at a carbon atom, $R_2$, $R_3$, $R_4$, $R_5$, $R_6$ and $R_8$ are each hydrogen and $R_7$ is nitro or a radical of formula II wherein $R_9$ is hydrogen, X is oxo, n is the number 0 and $R_{10}$ is pyridyl bonded at a carbon atom, phenyl that is unsubstituted or substituted by fluorine, chlorine, cyano, lower alkoxy, carboxy, lower alkyl or by 4-methyl-piper-azinyl-methyl, or $C_5$–$C_7$alkyl, thienyl or cyclohexyl, and to pharmaceutically acceptable salts thereof.

Preferred are especially compounds of formula I wherein $R_1$ is 4-pyridyl, N-oxido-4-pyridyl or 1H-indol-3-yl, and $R_7$ is fluoro-substituted alkoxy containing up to 2 carbon atoms, like preferably trifluoromethoxy or 1,1,2,2-tetrafluoroethoxy, and salts of such compounds containing at least one salt-forming group.

Most especially preferred are the compounds of formula I described in the Examples and pharmaceutically acceptable salts of such compounds having at least one salt-forming group.

In view of their inhibition of protein kinase C, greatest preference is given to those above-mentioned compounds of formula I wherein $R_4$ and $R_8$ are each hydrogen and the remaining substituents are as defined above, and to pharmaceutically acceptable salts of such compounds having at least one salt-forming group.

The compounds of formula I and salts of such compounds having at least one salt-forming group are prepared in accordance with processes known per se. The process according to the invention is as follows:

a) a compound of formula III

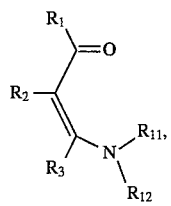

(III)

wherein $R_{11}$ and $R_{12}$ are each independently of the other lower alkyl and $R_1$, $R_2$ and $R_3$ are as defined above, functional groups present in a compound of formula III, with the exception of the groups participating in the reaction, being if necessary in protected form, or a salt of such a compound, is reacted with a compound of formula IV

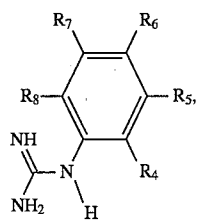

(IV)

wherein the substituents are as defined above, functional groups present in a compound of formula IV, with the exception of the guanidino group participating in the reaction, being if necessary in protected form, or with a salt of such a compound, and any protecting groups present are removed, or b) for the preparation of a compound of formula I wherein the radicals $R_4$, $R_5$, $R_6$, $R_7$ and $R_8$ are as defined above with the exception of nitro and fluoro-substituted lower alkoxy, a compound of formula V

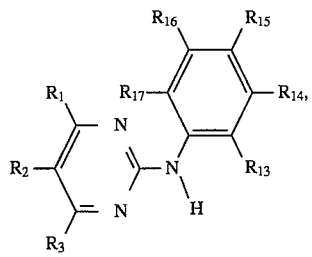

(V)

wherein one or two of the radicals $R_{13}$, $R_{14}$, $R_{15}$, $R_{16}$ and $R_{17}$ are each amino and the remaining radicals $R_{13}$, $R_{14}$, $R_{15}$, $R_{16}$ and $R_{17}$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy, and the remaining substituents are as defined above, functional groups present in a compound of formula V, with the exception of the amino group(s) participating in the reaction, being if necessary in protected form, is reacted with a compound of formula VI

HO—C(=X)—(Y)$_n$—$R_{10}$ (VI), wherein the substituents and symbols are as defined above, functional groups present in a compound of formula VI, with the exception of the HO—C(=X) group participating in the reaction, being if necessary in protected form, or with a reactive derivative of a compound of formula VI, and any protecting groups present are removed, or c) for the preparation of a compound of formula I wherein $R_1$ is pyridyl substituted at the nitrogen atom by oxygen, and wherein the other substituents and symbols are as defined above, a compound of formula I wherein $R_1$ is pyridyl is converted into the N-oxido compound with a suitable oxidising agent, and, if desired, a compound of formula I obtainable by any one of processes a to c is converted into its salt, or an obtainable salt of a compound of formula I is converted into the free compound.

The procedure for the above-mentioned process variants is explained in detail below:

General notes:

The end products of formula I may contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

Protecting groups, and the manner in which they are introduced and removed are described, for example, in "Protective Groups in Organic Chemistry", Plenum Press, London, N.Y. 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

Hydroxy-protecting groups are, for example, acyl radicals, such as unsubstituted or substituted, for example halo-substituted, lower alkanoyl, such as 2,2-dichloroacetyl, or acyl radicals of carbonic acid semiesters, especially tert-butoxycarbonyl, unsubstituted or substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, also trityl or formyl, or organic silyl or stannyl radicals, and also readily removable etherifying groups, such as tert-lower alkyl, for example tert-butyl, 2-oxa- or 2-thia-aliphatic or 2-oxa- or 2-thia-cycloaliphatic hydrocarbon radicals, especially 1-lower alkoxy-lower alkyl or 1-lower alkylthio-lower alkyl, for example methoxymethyl, 1-methoxy-ethyl, 1-ethoxy-ethyl, methylthiomethyl, 1-methylthioethyl or 1-ethylthioethyl, or 2-oxa- or 2-thiacycloalkyl having 5 or 6 ring atoms, for example tetrahydrofuryl or 2-tetrahydropyranyl or corresponding thia analogues, and unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

A protected amino group may be, for example, in the form of a readily clearable acylamino, arylmethylamino, etherified mercaptoamino, 2-acyl-lower alk-1-en-yl-amino, silylamino or stannylamino group or in the form of an azido group.

In a corresponding acylamino group, acyl is, for example, the acyl radical of an organic carboxylic acid having, for example, up to 18 carbon atoms, especially an alkanecarboxylic acid that is unsubstituted or substituted, for example, by halogen or by aryl, or of a benzoic acid that is unsubstituted or substituted, for example, by halogen, lower alkoxy or by nitro, or of a carbonic acid semiester. Such acyl groups are, for example, lower alkanoyl, such as formyl, acetyl or propionyl, halo-lower alkanoyl, such as 2-halo-acetyl, especially 2-chloro-, 2-bromo-, 2-iodo-, 2,2,2-trifluoro- or 2,2,2-trichloro-acetyl, benzoyl that is unsubstituted or substituted, for example, by halogen, lower alkoxy or by nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, arylmethoxycarbonyl having one or two aryl radicals which are preferably phenyl that is unsubstituted or mono- or poly-substituted, for example, by lower alkyl, especially tert-lower alkyl, such as tert-butyl, lower alkoxy, such as methoxy, hydroxy, halogen, for example chlorine, and/or by nitro, such as unsubstituted or substituted benzyloxycarbonyl, for example 4-nitro-benzyloxycarbonyl, or substituted diphenylmethoxycarbonyl, for example benzhydryloxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl wherein each of the substituents, independently of the others, is an aliphatic, araliphatic, cycloaliphatic or aromatic hydrocarbon radical having up to 15 carbon atoms that is unsubstituted or substituted, for example, by lower alkyl, lower alkoxy, aryl, halogen or by nitro, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as 2-triphenylsilylethoxycarbonyl.

Other acyl radicals that are suitable as amino-protecting groups are corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, unsubstituted or substituted, for example nitro-substituted, di(phenyl-lower alkyl)phosphoryl, for example dibenzylphosphoryl or di(4-nitrobenzyl)phosphoryl, unsubstituted or substituted phenoxy-phenyl-phosphonyl, for example phenoxyphenylphosphonyl, di-lower alkylphosphinyl, for example diethylphosphinyl, or unsubstituted or substituted diphenylphosphinyl, for example diphenylphosphinyl.

In an arylmethylamino group that is a mono-, di- or, especially, tri-arylmethylamino group, the aryl radicals are especially unsubstituted or substituted phenyl radicals. Such groups are, for example, benzyl-, diphenylmethyl- and especially trityl-amino.

An etherified mercapto group in an amino group protected by such a radical is especially arylthio or aryl-lower alkylthio, wherein aryl is especially phenyl that is unsubstituted or substituted, for example, by lower alkyl, such as methyl or tert-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that can be used as amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid semiesters, especially tert-butoxycarbonyl, benzyloxycarbonyl that is unsubstituted or substituted, for example, as indicated, for example 4-nitro-benzyloxycarbonyl, or diphenylmethoxycarbonyl, or 2-halo-lower alkoxycarbonyl, such as 2,2,2-trichloroethoxycarbonyl, also trityl or formyl. The removal of the protecting groups that are not constituents of the desired end product of formula I is effected in a manner known per se, for example by means of solvolysis, especially hydrolysis, alcoholysis or acidolysis, or by means of reduction, especially hydrogenolysis or chemical reduction, as desired stepwise or simultaneously.

A protected amino group is freed in a manner known per se and, according to the nature of the protecting groups, in various ways, preferably by means of solvolysis or reduction. 2-Halo-lower alkoxycarbonylamino (optionally after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can be cleaved also by treatment with a nucleophilic, preferably salt-forming, reagent, such as sodium thiophenolate, and 4-nitro-benzyloxycarbonylamino can be cleaved also by treatment with an alkali metal dithionite, for example sodium dithionite. Unsubstituted or substituted diphenylmethoxycarbonylamino, ten-lower alkoxycarbonylamino or 2-trisubstituted silylethoxycarbonylamino can be cleaved by treatment with a suitable acid, for example formic or trifluoroacetic acid; unsubstituted or substituted benzyloxycarbonylamino can be cleaved, for example, by means of hydrogenolysis, that is to say by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, optionally in the presence of water, and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and subsequent solvolysis, such as alcoholysis or hydrolysis, of the resulting condensation product. An amino group protected by 2-substituted silylethoxycarbonyl can also be convened into the free amino group by treatment with a salt of hydrofluoric acid yielding fluoride anions.

A hydroxy group protected by a suitable acyl group, an organic silyl group or by unsubstituted or substituted 1-phenyl-lower alkyl is freed analogously to a correspondingly protected amino group. Hydroxy protected by unsubstituted or substituted 1-phenyl-lower alkyl, for example benzyl, is preferably freed by catalytic hydrogenation, for example in the presence of a palladium-on-carbon catalyst. A hydroxy group protected by 2,2-dichloroacetyl is freed, for example, by basic hydrolysis, and a hydroxy group etherified by ten-lower alkyl or by a 2-oxa- or 2-thia-aliphatic or 2-oxa- or 2-thia-cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed by a salt of hydrofluoric acid yielding fluoride anions, for example tetrabutylammonium fluoride.

Process a:

Preferably $R_{11}$ and $R_{12}$ are each methyl.

Free functional groups in a compound of formula III that are advantageously protected by readily removable protecting groups are especially amino groups in the radical $R_1$ and the imino group of 1H-indolyl. The latter can be protected, for example, by benzyl.

Free functional groups in a compound of formula IV that are advantageously protected by readily removable protecting groups are especially amino groups, but also hydroxy and carboxy groups.

A salt of a compound of formula IV is preferably an acid addition salt, for example a nitrate or one of the acid addition salts mentioned for the end products of formula I.

The reaction is carded out in a suitable solvent or dispersing agent, for example a suitable alcohol, such as 2-methoxy-ethanol, or a suitable lower alkanol, for example isopropanol, at a temperature of from room temperature (approx. 20° C.) to 150° C., for example under reflux. Especially when the compound of formula IV is used in the form of a salt, that salt is converted into the free compound, preferably in situ, by the addition of a suitable base, such as an alkali metal hydroxide, for example sodium hydroxide.

It is preferable to use as starting materials compounds of formula IV wherein one or two of the radicals $R_4$, $R_5$, $R_6$, $R_7$ and $R_8$ are each nitro and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy.

The starting material of formula III is obtained by reacting a compound of formula VII

wherein the substituents are as defined above, with a compound of formula VIII

wherein $R_{18}$ and $R_{19}$ are each lower alkyl and the remaining substituents are as defined above, in a manner analogous to that described in the European Patent Application having the Publication No. 233461. Typical representatives of a compound of formula VIII are N,N-dimethylformamide-dimethylacetal and N,N-dimethylacetamide-dimethylacetal. The reaction is carried out with heating of the reactants of formulae VII and VIII for several hours, for example for from 4 to 24 hours, at a temperature of approximately from 50° C. to 150° C., in the absence or, if necessary, in the presence of a solvent.

The starting material of formula HI is alternatively obtained by reacting a compound of formula VII with an ester of the formula $R_3$—C(=O)—O—$CH_2$—$CH_3$ wherein $R_3$ is as defined above, and reacting the resulting product with an amine of the formula H—N($R_{11}$)—$R_{12}$ wherein the substituents are as defined above.

The starting material of formula IV is obtained in the form of an acid addition salt by reacting a compound of formula IX

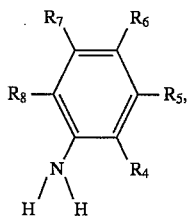

(IX)

wherein the substituents are as defined above, with cyanamide (NC—NH$_2$). The reaction is carried out in a suitable solvent or dispersing agent, for example a suitable alcohol, for example a suitable lower alkanol, such as ethanol, in the presence of equimolar amounts of the salt-forming acid at a temperature of from room temperature to 150° C., for example under reflux.

Process b:

Free functional groups in a compound of formula V or VI that are advantageously protected by readily removable protecting groups are especially amino groups, but also hydroxy and carboxy groups, that are not intended to participate in the desired reaction, for example amino in the radical R$_1$.

A reactive derivative of a compound of formula VI wherein X is oxo is especially a reactive (activated) ester, a reactive anhydride or a reactive cyclic amide. The same is true for the derivatives wherein X has one of the other definitions given above.

Reactive (activated) esters of an acid of formula VI are especially esters unsaturated at the linking carbon atom of the esterifying radical, for example esters of the vinyl ester type, such as actual vinyl esters (obtainable, for example, by transesterification of a corresponding ester with vinyl acetate; activated vinyl ester method), carbamoylvinyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonyl-phenol, 2,4,5-trichlorophenol, 2,3,4,5,6-pentachloro-phenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thio esters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), amino or amido esters (obtainable, for example, by treatment of the corresponding acid with an N-hydroxy-amino or N-hydroxy-amido compound, for example N-hydroxy-succinimide, N-hydroxy-piperidine, N-hydroxy-phthalimide or 1-hydroxy-benzotriazole, for example by the anhydride or carbodiimide method; activated N-hydroxy esters method), or silyl esters (which are obtainable, for example, by treatment of the corresponding acid with a silylating agent, for example hexamethyl disilazane, and react readily with hydroxy groups but not with amino groups).

Anhydrides of an acid of formula VI may be symmetric or preferably mixed anhydrides of that acid, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiderivatives, such as corresponding esters, for example carbonic acid lower alkyl semiesters (obtainable, for example, by treatment of the corresponding acid with haloformic, such as chloroformic, acid lower alkyl esters or with a 1-lower alkoxycarbonyl-2-lower alkoxy-1,2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), or anhydrides with organic acids, such as mixed anhydrides with organic carboxylic acids (obtainable, for example, by treatment of the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid, with a suitable organic sulfonic acid halide, such as lower alkane- or aryl-, for example methane- or p-toluene-sulfonic acid chloride; mixed sulfonic acid anhydrides method), and symmetric anhydrides (obtainable, for example, by condensation of the corresponding acid in the presence of a carbodiimide or of 1-diethylaminopropyne; symmetric anhydrides method).

Suitable cyclic amides are especially amides with five-membered diazacycles of aromatic character, such as amides with imidazoles, for example imidazole (obtainable, for example, by treatment of the corresponding acid with N,N'-carbonyldiimidazole; imidazolide method), or pyrazoles, for example 3,5-dimethyl-pyrazole (obtainable, for example, by way of the acid hydrazide by treatment with acetylacetone; pyrazolide method).

Derivatives of acids of formula VI that can be used as acylating agents can also be formed in situ. For example, N,N'-disubstituted amidino esters can be formed in situ by reacting a mixture of the starting material of formula V and the acid used as acylating agent in the presence of a suitable N,N-disubstituted carbodiimide, for example N,N'-dicyclohexylcarbodiimide. In addition, amino or amido esters of the acids used as acylating agents can be formed in the presence of the starting material of formula V to be acylated, by reacting a mixture of the corresponding acid and amino starting materials in the presence of an N,N'-disubstituted carbodiimide, for example N,N'-dicyclohexyl-carbodiimide, and an N-hydroxy-amine or N-hydroxy-amide, for example N-hydroxysuccinimide, where appropriate in the presence of a suitable base, for example 4-dimethylamino-pyridine.

The reaction is preferably carded out by reacting a reactive carboxylic acid derivative of a compound of formula VI with a compound of formula V wherein the amino group or hydroxy group participating in the reaction is in free form.

The reaction can be carded out in a manner known per se, the reaction conditions being dependent especially on whether, and if so how, the carboxy group of the acylating agent has been activated, usually in the presence of a suitable solvent or diluent or of a mixture thereof and, if necessary, in the presence of a condensation agent, which, for example when the carboxy group participating in the reaction is in the form of an anhydride, may also be an acid-binding agent, with cooling or heating, for example in a temperature range from approximately $-30°$ C. to approximately $+150°$ C., especially approximately from $0°$ C. to $+100°$ C., preferably from room temperature (approx. $+20°$ C.) to $+70°$ C., in an open or closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulfonate and 2-tert-butyl-5-methyl-isoxazolium perchlorate, or a suitable acylamino compound, for example 2-ethoxy- 1-ethoxycarbonyl- 1,2-dihydroquinoline. Customary acid-binding condensation agents are, for example, alkali metal carbonates or hydrogen carbonates, for example sodium or potassium carbonate or hydrogen carbonate (customarily together with a sulfate), or organic bases, such as, customarily, pyridine or sterically hindered tri-lower alkylamines, for example N,N-diisopropyl-N-ethyl-amine.

The starting material of formula V is obtained by reduction of the nitro group(s) in a compound of formula I wherein one or two of the radicals $R_4$, $R_5$, $R_6$, $R_7$ and $R_8$ are each nitro. That reduction can be carried out, for example, by catalytic hydrogenation in a suitable solvent, such as a suitable acyclic or cyclic ether, such as in tetrahydrofuran. There is preferably used as hydrogenation catalyst palladium on active carbon (5%) and in that case the hydrogenation is preferably carried out under normal pressure.

Process c:

A suitable oxidising agent for converting a compound of formula I wherein $R_1$ is pyridyl into the N-oxido compound is preferably a suitable peracid, for example a suitable perbenzoic acid, such as especially m-chloroperbenzoic acid. The reaction is carried out in an inert solvent, for example a halogenated hydrocarbon, such as preferably methylene chloride, at temperatures of approximately from $-20°$ C. to $+150°$ C., especially approximately from $0°$ C. to the boiling point of the solvent in question, in general below $+100°$ C., and preferably at room temperature or at slightly elevated temperature ($20°$ C.–$70°$ C.).

Acid addition salts of compounds of formula I are obtained in customary manner, for example by treatment with an acid or a suitable anion exchange reagent.

Acid addition salts can be convened into the free compounds in customary manner, for example by treatment with a suitable basic agent.

Mixtures of isomers can be separated into the individual isomers in a manner known per se, for example by fractional crystallisation, chromatography, etc.

The processes described above, including the processes for removing protecting groups and the additional process steps, are, unless otherwise indicated, carried out in a manner known per se, for example in the presence or absence of preferably inert solvents and diluents, if necessary in the presence of condensation agents or catalysts, at reduced or elevated temperature, for example in a temperature range of from approximately $-20°$ C. to approximately $150°$ C., especially from approximately $0°$ C. to approximately $+70°$ C., preferably from approximately $+10°$ C. to approximately $+50°$ C., and more especially at room temperature, in a suitable vessel and if necessary in an inert gas atmosphere, for example a nitrogen atmosphere.

In those process steps, taking account of all the substituents in the molecule, if necessary, for example when readily hydrolysable radicals are present, especially mild reaction conditions should be used, such as short reaction times, the use of mild acidic or basic agents at low concentrations, stoichiometric quantity ratios, and the selection of suitable catalysts, solvents, temperature and/or pressure conditions.

The invention relates also to those forms of the process in which a compound obtainable as intermediate at any stage of the process is used as starting material and the remaining steps are carried out or the process is interrupted at any stage or a starting material is formed under the reaction conditions or is used in the form of a reactive derivative or salt. It is preferable to begin with those starting materials which in accordance with the process result in the compounds described above as being especially valuable.

The present invention relates also to novel starting materials and/or intermediates and to processes for the preparation thereof. The starting materials used and the reaction conditions chosen are preferably those which result in the compounds described in this Application as being especially preferred.

The invention relates also to a method of treating warm-blooded animals suffering from a tumoral disease, which comprises administering to warm-blooded animals requiring such treatment an effective, tumour-inhibiting amount of a compound of formula I or of a pharmaceutically acceptable salt thereof. The invention relates further to the use of a compound of formula I or of a pharmaceutically acceptable salt thereof for inhibiting PDGF-receptor kinase or to the use of a compound of formula I wherein $R_4$, and $R_8$ are each hydrogen, or of a pharmaceutically acceptable salt thereof, for inhibiting protein kinase C in warm-blooded animals or for preparing pharmaceutical compositions for use in the therapeutic treatment of the human or animal body. Effective doses, for example daily doses of approximately from 1 to 1000 mg, especially from 50 to 500 mg, are administered to a warm-blooded animal of approximately 70 kg body weight according to species, age, individual condition, mode of administration and the individual syndrome.

The invention relates also to pharmaceutical compositions comprising an effective amount, especially an amount effective in the prevention or therapy of one of the abovementioned diseases, of the active ingredient together with pharmaceutically acceptable carriers that are suitable for topical, enteral, for example oral or rectal, or parenteral administration, and may be inorganic or organic, solid or liquid. For oral administration there are used especially tablets or gelatin capsules comprising the active ingredient together with diluents, for example lactose, dextrose, sucrose, mannitol, sorbitol, cellulose and/or glycerol, and/or lubricants, for example silicic acid, talc, stearic acid or salts thereof, such as magnesium or calcium stearate, and/or polyethylene glycol. Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. The pharmacologically active compounds of the present invention can also be used in the form of parenterally administrable compositions or in the form of infusion solutions. Such solutions are preferably isotonic aqueous solutions or suspensions, which, for example in the case of lyophilised compositions that comprise the active ingredient alone or together with a carder, for example mannitol, can be prepared before use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions which, if desired, may comprise further pharmacologically active substances, such as antibiotics, are prepared in a manner known per se, for example by means of conventional mixing, granulating, confectioning, dissolving or lyophilising processes, and comprise approximately from 1% to 100%, especially from approximately 1% to approximately 20%, active ingredient(s).

The following Examples illustrate the invention but do not limit the invention in any way. The $R_f$ values are determined on silica gel thin-layer plates (Merck, Darmstadt, Germany). The ratio to one another of the eluants in the eluant mixtures used is given in proportions by volume (v/v), and temperatures are given in degrees Celsius.

Abbreviations:

HV: high vacuum n: normal (straight-chain)

rotovap: rotary evaporator

RT: room temperature

EXAMPLE 1

41.3 g (0.17 mol) of 3-nitrophenyl-guanidine nitrate, made into a slurry in 50 ml of isopropanol, are added to a solution of 30 g (0.17 mol) of 3-dimethylamino-1-(3-pyridyl)- 2-propen-1-one [described in EP-A-0 233 461] in 250 ml of isopropanol. After the addition of 7.49 g (0.19 mol) of sodium hydroxide, the yellow suspension is boiled at reflux for 8 hours. After cooling to 0°, the mixture is filtered and washed with 200 ml of isopropanol. The filtration residue is made into a sherry in 300 ml of water and stirred for 30 minutes, filtered and washed with 200 ml of water. After again making into a slurry in 200 ml of ethanol and washing with 200 ml of ethanol/diethyl ether (1:1) there is obtained N-(3-nitrophenyl)-4-(3-pyridyl)-2-pyrimidine-amine; m.p. 212°–213°, $R_f$=0.75 (chlorofoform:menthol=9:1).

The starting material is obtained as follows:
Step 1.1

42 ml (0.6 mol) of nitric acid (65%) are added dropwise to a yellow suspension of 82.88 g (0.6 mol) of 3-nitroaniline in 200 ml of ethanol. After the exothermic reaction has subsided, 75.7 g (0.9 mol) of cyanamide (50% in water) are added and the reaction mixture is boiled at reflux for 21 hours. After cooling to 0°, the mixture is filtered and washed six times with ethanol/diethyl ether (1:1). Drying under HV at 40° yields 3-nitrophenyl-guanidine nitrate; m.p. 205°–207°.

Step 1.2

8 g (0.35 mol) of sodium are placed in 260 ml of toluene and at 100° made into a suspension using a vibromixer. After cooling to 0°, 17 ml (0.42 mol) of methanol are added dropwise, with cooling, and the mixture is then stirred for 45 minutes at 75°. At 25° and with ice-cooling, a solution of 38.5 ml (0.35 mol) of 3-acetylpyridine and 28 ml (0.35 mol) of ethyl formate in 300 ml of toluene are added dropwise in the course of 45 minutes. The yellow suspension is stirred for 16 hours at 25° and then 23.7 g (0.52 mol) of dimethylamine are added. After the addition of 100 ml of toluene, the mixture is stirred for 45 minutes at 25°, and then at 0° a solution of 20 ml of acetic acid in 150 ml of toluene is added dropwise in the course of 30 minutes and the mixture is then boiled at reflux for 1 hour. After cooling to 25°, the mixture is filtered and washed with 500 ml of toluene/hexane (1:1) and the filtrate is concentrated until crystallisation begins. Cooling to 0°, filtration and drying at 80° under HV yield 3-dimethylamino-1-(3-pyridyl)-2-propen-1one; m.p. 81°–82°.

EXAMPLE 2

100 mg (0.38 mmol) of N-(3-aminophenyl)-4-(3-pyridyl)-2-pyrimidine-amine are dissolved in 5 ml, of pyridine; 58.5 µl (0.46 mmol) of 4-chlorobenzoyl chloride are added and the mixture is stirred at room temperature for 24 hours. 10 ml of water are added to the reaction mixture which is then cooled to 0° and filtered. Washing with water and drying yield N-[3-(4-chlorobenzoylamido)-phenyl]-4-(3-pyridyl)-2-pyrimidine-amine; m.p. 238°–240°, $R_f$=0.66 (chloroform:methanol=9:1).

The starting material is obtained as follows:
Step 2.1

A suspension of 17.0 g (0.058 mol) of N-(3-nitrophenyl)-4-(3-pyridyl)- 2-pyrimidine-amine in 1700 ml of tetrahydrofuran is stirred with 1.7 g of palladium on active carbon (5%) under a hydrogen atmosphere at normal pressure for 21 hours. The suspension is filtered and the filtrate is concentrated in a rotary evaporator. The yellow solid product that remains behind is stirred overnight in 200 ml of methylene chloride. Filtration and drying yield N-(3-aminophenyl)-4-(3-pyridyl)-2-pyrimidine-amine; m.p. 89°–90°, $R_f$=0.38 (chloroform:methanol=9:1).

EXAMPLE 3

53 µl (0.46 mmol) of benzoyl chloride are added to a solution of 100 mg (0.38 mmol) of N-(3-aminophenyl)-4-(3-pyridyl)-2-pyrimidine-amine in 5 ml of pyridine and the mixture is stirred under a nitrogen atmosphere for 24 hours at room temperature. 10 ml of water are added to the reaction mixture which is then cooled to 0°, filtered and washed with water. Drying under HV yields N-(3-benzoylamidophenyl)-4-(3-pyridyl)-2-pyrimidine-amine; m.p. 207°–209°, $R_f$=0.53 (chloroform:methanol=9:1).

EXAMPLE 4

A solution of 100 mg (0.38 mmol) of N-(3-aminophenyl)-4-(3-pyridyl)-2-pyrimidine-amine and 59 mg (0.46 mmol) of 2-pyridinecarboxylic acid chloride in 5 ml of pyridine is stirred under nitrogen for 24 hours at room temperature. After the addition of 30 mg (0.23 mmol) of 2-pyridinecarboxylic acid chloride, the mixture is stirred for 18 hours and then a further 25 mg (0.19 mmol) of 2-pyridinecarboxylic acid chloride are added and the mixture is stirred for 72 hours at 25°. After the addition of 10 ml of water and cooling to 0°, the mixture is filtered and washed with water. Separation by chromatography (silica gel, CHCl$_3$/MeOH=9:1) yields N-[3-(2-pyridyl)-carboxamido-phenyl]-4-(3-pyridyl)-2-pyrimidine-amine; m.p. 187°–190°, $R_f$=0.58 (chloroform:methanol=9:1)

EXAMPLE 5

Analogously to Example 4, N-[3-(3-pyridyl)-carboxamido-phenyl]-4-(3-pyridyl)-2-pyrimidine-amine is prepared from 3-pyridinecarboxylic acid chloride; m.p. 217°–220°, $R_f$=0.29 (chloroform:methanol=9:1).

EXAMPLE 6

Analogously to Example 4, N-[3-(4-pyridyl)-carboxamido-phenyl]-4-(3-pyridyl)- 2-pyrimidine-amine is synthesised from 4-pyridinecarboxylic acid chloride; m.p. 224°–226°, $R_f$=0.29 (chloroform:methanol=9:1).

EXAMPLE 7

63 μl (0.46 mmol) of pentafluorobenzoyl chloride are added to a solution of 100 mg (0.38 mmol) of N-(3-aminophenyl)-4-(3-pyridyl)-2-pyrimidine-amine in 5 ml of pyridine and the mixture is stirred under nitrogen at room temperature for 17 hours. 10 ml of water are added to the brown reaction solution which is then cooled to 0° and filtered. The residue is recrystallised from ethanol/acetone and yields the crystalline product N-( 3-pentafluorobenzoylamido-phenyl)-4-(3-pyridyl)-2-pyrimidine-amine; m.p. 234°–244°, $R_f$=0.41 (chloroform:methanol 9:1).

EXAMPLE 8

28 mg (0.19 mmol) of phthalic acid anhydride are added to a solution of 50 mg (0.19 mmol) of N-(3-aminophenyl)-4-(3-pyridyl)-2-pyrimidine-amine in 1 ml of pyridine. After 2.5 hours, a further 14 mg (0.095 mmol) of phthalic acid anhydride are added to the yellow reaction solution and the mixture is stirred for 20 hours at 25°. The suspension is filtered and washed with a small amount of cold pyridine. The residue is digested with 2×2.5 ml of absolute ethanol and yields N-[3-(2-carboxybenzoylamido)phenyl]-4-(3-pyridyl)-2-pyrimidine-amine; m.p. 206°–209°, $R_f$=0.07 (chloroform:methanol =9:1).

EXAMPLE 9

A solution of 100 mg (0.38 mmol) of N-(3-aminophenyl)-4-(3-pyridinyl)-2-pyrimidine-amine and 105 μl (0.46 mmol) of caproic acid anhydride in 5 ml of pyridine is stirred under a nitrogen atmosphere for 24 hours at 25° and then concentrated in a rotary evaporator. The residue is purified by flash chromatography (silica gel, chloroform:methanol 95:5), yielding N-(3-n-hexanoylamido-phenyl)-4-(3-pyridyl)-2-pyrimidineamine; m.p. 180°–184°, $R_f$=0.78 (chloroform:methanol=9:1).

EXAMPLE 10

1 g (5.68 mmol)of 3-dimethylamino-1-(2-pyridyl)-2-propen-1-one [EP-A-233 461] is dissolved in 8 ml of isopropanol, and 1.38 g (5.68 mmol) of 3-nitrophenylguanidine nitrate are added. After the addition of 0.25 g (6.24 mmol) of sodium hydroxide, the yellow suspension is heated at reflux for 20 hours, then cooled to 0°, filtered and washed with 30 ml of isopropanol. The filtration residue is stirred in 15 ml of ethanol for 20 minutes, filtered and washed with a small amount of cold ethanol, yielding N-(3-nitrophenyl)-4-(2-pyridyl)-2-pyrimidine-amine; m.p. 213°–219°.

EXAMPLE 11

1.38 g (5.68 mmol) of 3-nitrophenyl-guanidine nitrate and 0.25 g (6.24 mmol) of sodium hydroxide are added to a solution of 1 g (5.68 mmol) of 3-dimethylamino-1-(4-pyridyl)-2-propen-1-one [U.S. Pat. No. 4,281,000] in 8 ml of isopropanol. The yellow suspension is heated at reflux for 20 hours and then cooled to 0°. After washing with 30 ml of isopropanol the filtration residue is made into a slurry in succession in 15 ml of ethanol and then in 15 ml of water and filtered each time. Drying under HV yields N-(3-nitrophenyl)-4-(4-pyridyl)-2-pyrimidine-amine; m.p. 282°–284°.

EXAMPLE 12

Analogously to Example 2, N-[3-(2-methoxybenzoylamido)-phenyl]-4-(3-pyridyl)- 2-pyrimidine-amine is prepared from 2-methoxybenzoyl chloride; m.p. 115°–117°, $R_f$=0.76 (chloroform:methanol=9:1).

EXAMPLE 13

Analogously to Example 2, N-[3-(4-fluorobenzoylamido)-phenyl]-4-(3-pyridyl)- 2-pyrimidine-amine is prepared from 4-fluorobenzoyl chloride; m.p. 215°–216°, $R_f$=0.34 (chloroform:methanol=9:1).

EXAMPLE 14

Analogously to Example 2, N-[3-(4-cyanobenzoylamido)-phenyl]-4-(3-pyridyl)- 2-pyrimidine-amine is prepared from 4-cyanobenzoyl chloride; m.p. 220°–222°, $R_f$=0.31 (chloroform:methanol=9:1).

EXAMPLE 15

Analogously to Example 2, N-[3-(2-thienylcarboxamido)-phenyl]-4-(3-pyridyl)- 2-pyrimidine-amine is prepared from 2-thiophenecarboxylic acid chloride; m.p. 139°–141°, $R_f$=0.35 (chloroform:methanol=9:1).

EXAMPLE 16

Analogously to Example 2, N-(3-cyclohexyl-carboxamido-phenyl)-4-(3-pyridyl)- 2-pyrimidine-amine is prepared from cyclohexanecarboxylic acid chloride; m.p. 205°–206°, $R_f$=0.36 (chloroform:methanol=9:1).

EXAMPLE 17

Analogously to Example 2, N-[3-(4-methylbenzoylamido)-phenyl]-4-(3-pyridyl)- 2-pyrimidine-amine is prepared from 4-methylbenzoyl chloride; m.p. 214°–216°, $R_f$=0.64 (chloroform:methanol=9:1).

EXAMPLE 18

Analogously to Example 2, N-[3-(4-chloro-benzoylamido)-phenyl]-4-(4-pyridyl)- 2-pyrimidine-amine is prepared by treatment of 100 mg (0.38 mmol) of N-(3-aminophenyl)- 4-(4-pyridyl)-2-pyrimidine-amine with 58 μl (0.46 mmol) of 4-chlorobenzoyl chloride; m.p. 258°–261°; $R_f$=0.37 (CHCl$_3$:methanol=9:1).

The starting material is obtained as follows:
Step 18.1

Analogously to Step 2.1, N-(3-aminophenyl)-4-(4-pyridyl)-2-pyrimidine-amine is obtained by treatment of 300 mg(1.0 mmol) of N-(3-nitrophenyl)-4-(4-pyridyl)-2-pyrimidine-amine (see Example 11) under a hydrogen atmosphere; m.p. 200°–202°, $R_f$=0.27 (CHCl$_3$:methanol=95:5).

EXAMPLE 19

Analogously to Example 2, N-{3-[4-(4-methylpiperazinomethyl)-benzoylamido]-phenyl}- 4-(3-pyridyl)-2-pyrimidine-amine is prepared from 98 mg (0.3 mmol) of 4-(4-methyl-piperazinomethyl)-benzoyl chloride; m.p. 198°–201°.

EXAMPLE 20

A solution of 8.0 g (28.85 mmol) of N-(5-amino-2-methylphenyl)-4-(3-pyridyl)- 2-pyrimidine-amine and 4.0 ml (34.6 mmol) of benzoyl chloride in 320 ml of pyridine are stirred under nitrogen at room temperature for 23 hours. The reaction mixture is concentrated under HV; 200 ml of water are added and, after cooling to 0°, the mixture is filtered. After drying at 80° under HV, the crude product is made into a slurry with $CH_2Cl_2$/methanol (95:5) and filtered, yielding N-(5-benzoylamido-2-methylphenyl)-(3-pyridyl)-2-pyrimidine-amine. After separation by chromatography there are obtained further amounts of that product; m.p. 173°–176°, $R_f$=0.65 ($CHCl_3$:methanol=9:1).

The starting material is obtained as follows:
Step 20.1

9.1 ml (0.13 mol) of 65% nitric acid are added dropwise in the course of 5 minutes to a yellow suspension of 20.0 g (0.13 mol) of 2-amino-4-nitrotoluene in 50 ml of absolute ethanol. When the exothermic reaction has subsided, 8.32 g (0.198 mol) of cyanamide dissolved in 8.3 ml of water are added. The brown reaction mixture is boiled at reflux for 25 hours, cooled to 0° and filtered. Washing with 4×100 mi of ethanol/diethyl ether (1:1) and drying yield 2-methyl-5-nitrophenyl-guanidine nitrate; m.p. 219°–226°.
Step 20.2

248.2 g (0.96 mol) of 2-methyl-5-nitrophenylguanidine nitrate are added to a solution of 170 g (0.96 mol) of 3-dimethylamino-1-(3-pyridyl)-2-propen-1-one in 2.0 liters of isopropanol. After the addition of 42.5 g of sodium hydroxide, the reddish suspension is boiled at reflux for 12 hours. After cooling to 0°, filtration, washing with 2.0 liters of isopropanol and 3×400 ml of methanol and drying, there is obtained N-(2-methyl-5-nitrophenyl)- 4-(3-pyridyl)-2-pyrimidine-amine, m.p. 195°–198°, $R_f$=0.68 (methylene chloride:methanol=9.1).
Step 20.3

A suspension of 143.0 g (0.46 mol) of N-(2-methyl-5-nitrophenyl)-4-(3-pyridyl)- 2-pyrimidine-amine in 7.15 liters of ethyl acetate is stirred with 14.3 g of palladium on active carbon (10% Pd) under a hydrogen atmosphere at normal pressure for 6.5 hours. The suspension is filtered and the filtrate is concentrated in a rotary evaporator. The crude product is recrystallised from methylene chloride, yielding N-(5-amino-2-methylphenyl)- 4-(3-pyridyl)-2-pyrimidine-amine; m.p. 138°–140°, $R_f$=0.36 (methylene chloride:methanol=9:1).

EXAMPLE 21

Analogously to Example 20, N-{5-[4-(4-methyl-piperazinomethyl)-benzoylamido]-2-methylphenyl}-4-(3-pyridyl)-2-pyrimidine-amine is prepared from 10.68 g (32.8 mmol) of 4-(4-methyl-piperazinomethyl)-benzoyl chloride; m.p. 211°–213°, $R_f$=0.33 (methylene chloride:methanol:25% aqueous ammonia solution=95:5:1).

EXAMPLE 22

Analogously to Example 20, N-[5-(4-methyl-benzoylamido)-2-methylphenyl]-4-(3-pyridyl)-2-pyrimidine-amine is prepared from 0.23 ml (1.7 mmol) of p-toluoyl chloride (p-toluyl chloride); m.p. 102°–106°, Re=0.4 (methylene chloride:methanol=9:1).

EXAMPLE 23

Analogously to Example 20, N-[5-(2-naphthoylamido)-2-methylphenyl]-4-(3-pyridyl)-2-pyrimidine-amine is prepared from 330 mg (1.73 mmol) of 2-naphthoyl chloride; m.p. 97°–101°, $R_f$=0.45 (methylene chloride:methanol=9:1).

EXAMPLE 24

Analogously to Example 20, N-[5-(4-chloro-benzoylamido)-2-methylphenyl]-4-(3-pyridyl)-2-pyrimidine-amine is synthesised from 0.22 ml (1.73 mmol) of 4-chlorobenzoyl chloride; m.p. 216°–219°, $R_f$ =0.39 (methylene chloride:methanol=9:1).

EXAMPLE 25

Analogously to Example 20, N-[5-(2-methoxy-benzoylamido)-2-methylphenyl]-4-(3-pyridyl)-2-pyrimidine-amine is prepared from 0.28 ml (1.87 mmol) of 2-methoxybenzoyl chloride; m.p. 88°–92°, $R_f$=0.45 (methylene chloride:methanol=9:1).

EXAMPLE 26

Analogously to Example 1, N-(3-trifluoromethoxy-phenyl)-4-(3-pyridyl)-2-pyrimidine-amine is obtained from 1.0 g (5.68 mmol) of 3-dimethylamino-1-(3; -pyridyl)-2-propen-1-one and 1.53 g (5.68 mmol) of 3-trifluoromethoxyphenyl-guanidine nitrate; $R_f$=0.7 (chloroform:methanol=9:1).

The starting material is obtained as follows:
Step 26.1

Analogously to Step 1.1, 3-trifluoromethoxy-phenyl-guanidine nitrate is prepared from 2.0 g (11.3 mmol) of 3-trifluoromethoxy-aniline and 1.4 g (16.6 mol) of cyanamide (50% in water); $R_f$=0.1 (methylene chloride:methanol:25% aqueous ammonia solution=150:10:1).

EXAMPLE 27

Analogously to Example 1, N-(3-[1,1,2,2-tetrafluoroethoxy]-phenyl)-4-(3-pyridyl)- 2-pyrimidine-amine is obtained from 1.0 g (5.68 mmol) of 3-dimethylamino-1-(3-pyridyl)-2-propen- 1-one and 1.78 g (5.68 mmol) of 3-(1,1,2,2-tetrafluoroethoxy)-phenyl-guanidine nitrate; $R_f$=0.75 (chloroform:methanol=9:1).

The starting material is obtained as follows:
Step 27.1

Analogously to Step 1.1, 3-(1,1,2,2-tetrafluoro-ethoxy)-phenyl-guanidine nitrate is prepared from 2.09 g (10 mmol) of 3-(1,1,2,2-tetrafluoroethoxy)-aniline and 1.26 g (15 mol) of cyanamide (50% in water); $R_f$=0.15 (methylene chloride:methanol:25% aqueous ammonia solution=150:10:1).

EXAMPLE 28

Analogously to Example 1, N-(3-nitro-5-methyl-phenyl)-4-(3-pyridyl)-2-pyrimidine-amine is obtained from 1.0 g (5.68 mmol) of 3-dimethylamino-1-(3-pyridyl)-2-propen-1-one and 1.46 g (5.68 mmol) of 3-nitro-5-methylphenyl-guanidine nitrate; $R_f$=0.72 (chloroform:methanol=9:1).

The starting material is obtained as follows:
Step 28.1

Analogously to Step 1.1, 3-nitro-5-methyl-phenyl-guanidine nitrate is prepared from 1.52 g (10 mmol) of 3-nitro-5-methylaniline and 1.26 g (15 mol) of cyanamide (50% in water); $R_f$=0.1 (methylene chloride:methanol:25% aqueous ammonia solution=150:10:1).

EXAMPLE 29

Analogously to Example 1, N-(3-nitro-.5-trifluoromethylphenyl)-4-(3-pyridyl)- 2-pyrimidine-amine is obtained from 1.0 g (5.68 mmol) of 3-dimethylamino-1-(3-pyridyl)-2-propen-1-one and 1.76 g (5.68 mmol)of 3-nitro-5-trifluoromethylphenyl-guanidine nitrate; $R_f$=0.8 (chloroform:methanol=9:1).

The starting material is obtained as follows:
Step 29.1
Analogously to Step 1.1, 3-nitro-5-trifluoromethylphenyl-guanidine nitrate is prepared from 2.06 g (10 mmol) of 3-nitro-5-trifluoromethylaniline and 1.26 g (15 mol) of cyanamide (50% in water); $R_f$=0.2 (methylene chloride:methanol:25% aqueous ammonia solution=150:10:1).

EXAMPLE 30

200 mg (0.68 mmol) of N-(3-nitrophenyl)-4-(3-pyridyl)-2-pyrimidine-amine are suspended in 5 ml of methylene chloride, and 225 mg (0.71 mmol) of 3-chloroperbenzoic acid are added. After 2 hours a further 10 ml of methylene chloride are added. The suspension is stirred for a further 20 hours at room temperature. Filtration and flash chromatography of the residue (methylene chloride:methanol:25% aqueous ammonia solution=90:10:1) yield N-(3-nitro-phenyl)-4-(N-oxido-3-pyridyl)-2-pyrimidine-amine; $R_f$=0.4 (methylene chloride:methanol:25% aqueous ammonia solution=90: 10:1), m.p. 252°–258°.

EXAMPLE 31

150 mg (0.39 mmol) of N-(3-benzoylamido-5-methylphenyl)-4-(3-pyridyl)-2-pyrimidine-amine are suspended in 6 ml of methylene chloride, and 129 mg (0.41 mmol) of 3-chloroperbenzoic acid are added. After 22 hours, the mixture is filtered and the residue is purified by flash chromatography (methylene chloride:methanol:25% aqueous ammonia solution=90:10:1), yielding N-(3-.benzoylamido-5-methylphenyl)-4-(N-oxido-3-pyridyl)-2-pyrimidine-amine; $R_f$=0.3 (methylene chloride:methanol:25% aqueous ammonia solution=90:10:1), m.p. 295°–300°.

EXAMPLE 32

To a solution of 13.2 g (75 mmol) of 3-dimethylamino-1-(4-pyridyl)-2-propen- 1-one [described in EP-A-0 233 461] in 500 ml of isobutanol are added 23.6 g (75 mmol) of 3-(1,1,2,2-tetrafluoroethoxy)phenylguanidine nitrate. Following the addition of 4 g (100 mmol) of sodium hydroxide, the reaction mixture is stirred for 3 hours at 110° C. The suspension is concentrated under reduced pressure, the residue is dissolved in 500 ml of methylene chloride/tetrahydrofuran (1:1), and the solution is extracted with 300 ml of water. The organic phase is dried over sodium sulfate and concentrated on a rotovap. Recrystallisation from diethyl ether/tetrahydrofuran gives N-[3-(1,1,2,2-tetrafluoroethoxy)phenyl]-4-(4-pyridyl)-2-pyrimidine-amine; $R_f$=0.9 (methylene chloride:methanol =9:1), FAB-MS: 365 ($M^+$+1), m.p. 191°–192°.

The starting material is obtained as follows:
Step 32.1
To a suspension of 25.2 g (120 mmol) of 3-(1,1,2,2-tetrafluoroethoxy)aniline in 125 ml of ethanol are added 10.1 g (240 mmol) of cyanamide (50% in water). Then 16.3 ml (192 mmol) of concentrated hydrochloric acid are added to the brown solution and the mixture is refluxed for 19 hours. After cooling to room temperature, the reaction mixture is concentrated under reduced pressure and the residue is dissolved in 80 ml of water. After addition of 19.2 g (240 mmol) of ammonium nitrate, the product is isolated by filtration, washed with water and dried at 60° C. under HV, giving 3-(1,1,2,2-tetrafluoroethoxy)phenylguanidine nitrate; m.p. 132°–134° C.

EXAMPLE 33

In accordance with the general procedure described in Example 32, reaction of 213 mg(1 mmol) of 3-dimethylamino-1-(3-indolyl)-2-propen- 1-one [described in EP-A-0 233 461] and 310 mg (1 mmol) of 3-(1,1,2,2-tetrafluoroethoxy)phenylguanidine nitrate gives N-[3-(1,1,2,2-tetrafluoroethoxy)phenyl]-4-(3-indolyl)-2-pyrimidine-amine; m.p. 140°–142°, FAB-MS: 403 ($M^+$+1).

EXAMPLE 34

500 mg (1.37 mmol)of N-[3-(1,1,2,2-tetrafluoroethoxy)phenyl]-4-(4-pyridyl)- 2-pyrimidine-amine are suspended in 10 ml of methylene chloride and to the suspension are added 430 mg(1.37 mmol) of m-chloroperbenzoic acid and the reaction mixture is stirred for 4 hours at RT. After extraction with water and 2N sodium hydroxide solution, the organic phase is dried and concentrated on a rotovap. Chromatography (methylene chloride:methanol=19:1 to 9:1) and subsequent crystallisation (methylene chloride:diethyl ether) give N-[3-(1,1,2,2-tetrafluoroethoxy)phenyl]-4-(N-oxido-4-pyridyl)-2-pyrimidine-amine in the form of lemon yellow crystals; FAB-MS: 381 ($M^+$+H), m.p. 191°–192°.

EXAMPLE 35

Tablets comprising 20 mg of active ingredient, for example one of the compounds of formula I described in Examples 1 to 34 and having the following composition are prepared in customary manner:

| Composition: | |
|---|---|
| active ingredient | 20 mg |
| wheat starch | 60 mg |
| lactose | 50 mg |
| colloidal silicic acid | 5 mg |
| talc | 9 mg |
| magnesium stearate | 1 mg |
| | 145 mg |

Preparation
The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plastic mass is obtained.

The plastic mass is pressed through a sieve of about 3 mm mesh size and dried, and the resulting dry granules are again forced through a sieve. Then the remainder of the wheat starch, the talc and the magnesium stearate are mixed in and the mixture is compressed to form tablets weighing 145 mg and having a breaking notch.

EXAMPLE 36

Tablets comprising 1 mg of active ingredient, for example one of the compounds of formula I described in Examples 1 to 34, and having the following composition are prepared in customary manner:

| Composition: | |
|---|---|
| active ingredient | 1 mg |
| wheat starch | 60 mg |
| lactose | 50 mg |
| colloidal silicic acid | 5 mg |
| talc | 9 mg |
| magnesium stearate | 1 mg |
| | 126 mg |

Preparation

The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plastic mass is obtained.

The plastic mass is pressed through a sieve of about 3 mm mesh size and dried, and the resulting dry granules are again forced through a sieve. Then the remainder of the wheat starch, the talc and the magnesium stearate are mixed in and the mixture is compressed to form tablets weighing 126 mg and having a breaking notch.

EXAMPLE 37

Capsules comprising 10 mg of active ingredient, for example one of the compounds of formula I described in Examples 1 to 34, are prepared in customary manner as follows:

| Composition: | |
|---|---|
| active ingredient | 2500 mg |
| talc | 200 mg |
| colloidal silicic acid | 50 mg |

Preparation

The active ingredient is intimately mixed with the talc and the colloidal silicic acid and the mixture is forced through a sieve of 0.5 mm mesh size and then introduced in 11 mg portions into hard gelatin capsules of a suitable size.

What is claimed is:

1. An N-phenyl-2-pyrimidine-amine compound of formula I

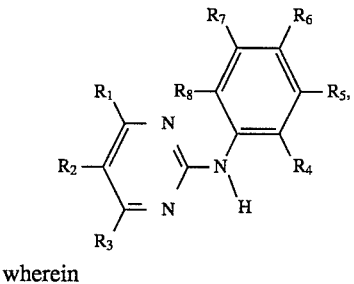

wherein $R_1$ is 4-pyrazinyl, 1-methyl-1H-pyrrolyl, amino- or amino-lower alkyl-substituted phenyl wherein the amino group in each case is free, alkylated or acylated, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one or two of the radicals $R_4$, $R_5$, $R_6$, $R_7$ and $R_8$ are each nitro, fluoro-substituted lower alkoxy or a radical of formula II $$-N(R_9)-C(=X)-(Y)_n-R_{10} \quad (II)$$

wherein $R_9$ is hydrogen or lower alkyl,

X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or hetero-cyclicaliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, or a salt of such a compound having at least one salt-forming group.

2. A compound of formula I according to claim 1, wherein one or two of the radicals $R_4$, $R_5$, $R_6$, $R_7$ and $R_8$ are each nitro or a radical of formula II wherein $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms or an aromatic, aromatic-aliphatic, cycloaliphatic, cycloaliphatic-aliphatic, heterocyclic or hetero-cyclicaliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterifed hydroxy, free, alkylated or acylated amino or free or esterified carboxy, and the remaining substituents are as defined in claim 1, or a salt of such a compound having at least one salt-forming group.

3. A compound of formula I according to claim 1, wherein $R_1$ is 4-pyrazinyl, 1-methyl-1H-pyrrolyl, amino- or amino-lower alkyl-substituted phenyl wherein the amino group in each case is free, alkylated by one or two lower alkyl radicals or acylated by lower alkanoyl or by benzoyl, 1H-indolyl or 1H-imidazolyl bonded at a five-membered ring carbon atom, or unsubstituted or lower alkyl-substituted pyridyl bonded at a ring carbon atom and unsubstituted or substituted at the nitrogen atom by oxygen, $R_2$ and $R_3$ are each independently of the other hydrogen or lower alkyl, one or two of the radicals $R_4$, $R_5$, $R_6$, $R_7$ and $R_8$ are each nitro, fluoro-substituted lower alkoxy or a radical of formula II wherein $R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic hydrocarbon radical having 5–22 carbon atoms, a phenyl or naphthyl radical each of which is unsubstituted or substituted by cyano, lower alkyl, hydroxy-lower alkyl, amino-lower alkyl, (4-methyl-piperazinyl)-lower alkyl, trifluoromethyl, hydroxy, lower alkoxy, lower alkanoyloxy, halogen, amino, lower alkylamino, di-lower alkylamino, lower alkanoylamino, benzoylamino, carboxy or by lower alkoxycarbonyl, or phenyl-lower alkyl wherein the phenyl radical is unsubstituted or substituted as indicated above, a cycloalkyl or cycloalkenyl radical having up to 30 carbon atoms, cycloalkyl-lower alkyl or cycloalkenyl-lower alkyl each having up to 30 carbon atoms in the cycloalkyl or cycloalkenyl moiety, a monocyclic radical having 5 or 6 ring members and 1–3 ring hetero atoms selected from nitrogen, oxygen and sulfur, to which radical one or two benzene radicals may be fused, or lower alkyl substituted by such a monocyclic radical, and the remaining radicals $R_4$, $R_5$, $R_6$, $R_7$ and $R_8$ are each independently of the others hydrogen, lower alkyl that is unsubstituted or substituted by amino, lower alkylamino, di-lower alkylamino, piperazinyl, piperidinyl, pyrrolidinyl or by morpholinyl, or lower alkanoyl, trifluoromethyl, hydroxy, lower alkoxy, lower alkanoyloxy, halogen, amino, lower alkylamino, di-lower alkylamino, lower alkanoylamino, benzoylamino, carboxy or lower alkoxycarbonyl, or a salt of such a compound having at least one salt-forming group.

4. A compound of formula I according to claim 1, wherein $R_1$ is pyridyl bonded at a ring carbon atom and unsubstituted or substituted at the nitrogen atom by oxygen, $R_2$ and $R_3$ are each hydrogen, $R_4$ is hydrogen or lower alkyl, $R_5$ is hydrogen, lower alkyl or fluoro-substituted lower alkoxy, $R_6$ is hydrogen, $R_7$ is nitro, fluoro-substituted lower alkoxy or a radical of formula II wherein $R_9$ is hydrogen, X is oxo, n is 0 and $R_{10}$ is an aliphatic hydrocarbon radical having 5–22 carbon atoms, a phenyl radical that is unsubstituted or substituted by cyano, lower alkyl, (4-methyl-piperazinyl)-lower alkyl, lower alkoxy, halogen or by carboxy; a cycloalkyl radical having up to 30 carbon atoms or a monocyclic radical having 5 or 6 ring members and 1–3 sulfur ring atoms, and $R_8$ is hydrogen, or a pharmaceutically acceptable salt of such a compound having at least one salt-forming group.

5. A compound of formula I according to claim 1, wherein $R_1$ is pyridyl or N-oxido-pyridyl each of which is bonded at a carbon atom, $R_2$ and $R_3$ are each hydrogen, $R_4$ is hydrogen or lower alkyl, $R_5$ is hydrogen, lower alkyl or trifluoromethyl, $R_6$ is hydrogen, $R_7$ is nitro, fluoro-substituted lower alkoxy or a radical of formula II wherein $R_9$ is hydrogen, X is oxo, n is the number 0 and $R_{10}$ is pyridyl bonded at a carbon atom, phenyl that is unsubstituted or substituted by halogen, cyano, lower alkoxy, carboxy, lower alkyl or by 4-methyl-piperazinylmethyl, or $C_5$–$C_7$alkyl, thienyl, 2-naphthyl or cyclohexyl, and $R_8$ is hydrogen, or a pharmaceutically acceptable salt of such a compound having at least one salt-forming group.

6. A compound according to claim 1 of formula I, wherein $R_4$ and $R_8$ are each hydrogen and the remaining substituents are as defined in claim 1, or a pharmaceutically acceptable salt of such a compound having at least one salt-forming group.

7. A compound according to claim 3 of formula I, wherein $R_4$ and $R_8$ are each hydrogen and the remaining substituents are as defined in claim 3, or a pharmaceutically acceptable salt of such a compound having at least one salt-forming group.

8. A compound according to claim 4 of formula I, wherein $R_4$ and $R_8$ are each hydrogen and the remaining substituents are as defined in claim 4, or a pharmaceutically acceptable salt of such a compound having at least one salt-forming group.

9. A compound according to claim 5 of formula I, wherein $R_4$ and $R_8$ are each hydrogen and the remaining substituents are as defined in claim 5, or a pharmaceutically acceptable salt of such a compound having at least one salt-forming group.

10. A compound according to claim 1 of formula I, wherein at least one of the radicals $R_4$ and $R_8$ is lower alkyl, and the remaining substituents are as defined in claim 1, or a pharmaceutically acceptable salt of such a compound having at least one salt-forming group.

11. A compound according to claim 3 of formula I, wherein at least one of the radicals $R_4$ and $R_8$ is lower alkyl, and the remaining substituents are as defined in claim 3, or a pharmaceutically acceptable salt of such a compound having at least one salt-forming group.

12. A compound according to claim 4 of formula I, wherein at least one of the radicals $R_4$ and $R_8$ is lower alkyl, and the remaining substituents are as defined in claim 4, or a pharmaceutically acceptable salt of such a compound having at least one salt-forming group.

13. A compound according to claim 5 of formula I, wherein at least one of the radicals $R_4$ and $R_8$ is lower alkyl, and the remaining substituents are as defined in claim 5, or a pharmaceutically acceptable salt of such a compound having at least one salt-forming group.

14. A compound according to claim 1 of formula I, wherein $R_1$ is pyridyl bonded at a carbon atom, $R_2$, $R_3$, $R_4$, $R_5$, $R_6$ and $R_8$ are each hydrogen and $R_7$ is nitro or a radical of formula II wherein $R_9$ is hydrogen, X is oxo, n is the number 0 and $R_{10}$ is pyridyl bonded at a carbon atom, phenyl that is unsubstituted or substituted by fluorine, chlorine, cyano, lower alkoxy, carboxy, lower alkyl or by 4-methyl-piperazinyl-methyl, or $C_5$–$C_7$alkyl, thienyl or cyclohexyl, or a pharmaceutically acceptable salt thereof.

15. A compound according to claim 1 of formula I, wherein $R_1$ is 4-pyridyl, N-oxido-4-pyridyl, or 3-indolyl, and $R_7$ is fluoro-substituted alkoxy containing up to 2 carbon atoms, or a salt of such a compound containing at least one salt-forming group.

16. A compound of formula I according to claim 1, wherein $R_1$ is 4-pyridyl, N-oxido-4-pyridyl, or 3-indolyl, and $R_7$ is trifluoromethoxy or 1,1,2,2-tetrafluoroethoxy, or a salt of such a compound containing at least one salt-forming group.

17. N-(5-Benzoylamido-2-methyl-phenyl)-4-(3-pyridyl)-2-pyrimidine-amine or a pharmaceutically acceptable salt thereof according to claim 1.

18. N-[3-(1,1,2,2-Tetrafluoroethoxy)phenyl]-4-(4-pyridyl)-2-pyrimidine-amine or a pharmaceutically acceptable salt thereof according to claim 1.

19. A compound according to claim 1 of the formula I or a pharmaceutically acceptable salt of such a compound having at least one salt-forming group selected from N-(3-Nitro-phenyl)-4-(3-pyridyl)-2-pyrimidine-amine, N-[3-(4-Chlorobenzoylamido)-phenyl]-4-(3-pyridyl)-2-pyrimidine-amine, N-(3-Benzoylamido-phenyl)-4-(3-pyridyl)-2-pyrimidine-amine, N-[3-(2-Pyridyl)carboxamido-phenyl]-4-(3-pyridyl)-2-pyrimidine-amine, N-[3-(3-pyridyl)carboxamido-phenyl]-4-(3-pyridyl)-2-pyrimidine-amine, N-[3-(4-pyridyl)carboxamido-phenyl]-4-(3-pyridyl)-2-pyrimidine-amine, N-(3-Pentafluoro-benzoylamido-phenyl)-4-(3-pyridyl)-2-pyrimidine-amine, N-[3-(2-Carboxy-benzoylamido )-phenyl]-4-(3-pyridyl)-2-pyrimidine-amine, N-(3-n-Hexanoylamido-phenyl)-4-(3-pyridyl)-2-pyrimidine-amine, N-(3-Nitro-phenyl)-4-(2-pyridyl)-2-pyrimidine-amine, N-(3-Nitro-phenyl)-4-(4-pyridyl)-2-pyrimidine-amine, N-[3-(2-Methoxy-benzoylamido)-phenyl]-4-(3-pyridyl)-2-pyrimidine-amine, N-[3-(4-Fluoro-benzoylamido)-phenyl]-4-(3-pyridyl)-2-pyrimidine-amine, N-[3-(4-Cyano-benzoylamido)-phenyl]-4-(3-pyridyl)-2-pyrimidine-amine, N-[3-(2-Thienylcarboxamido)-phenyl]-4-(3-pyridyl)-2-pyrimidine-amine, N-(3-Cyclohexycarboxamido-phenyl)-4-(3-pyridyl)-2-pyrimidine-amine, N-[3-(4-Methyl-benzoylamido)-phenyl]-4-(3-pyridyl)-2-pyrimidine-amine, N-[3-(4-Chloro-benzoylamido)-phenyl]-4-(4-pyridyl)-2-pyrimidine-amine, N-{3-[4-(4-Methyl-piperazinomethyl)-benzoylamido]-phenyl}-4-(3-pyridyl)- 2-pyrimidine-amine, N-[5-(4-Methyl-benzoylamido)-2-methyl-phenyl]-4-(3-pyridyl)-2-pyrimidine-amine, N-[5-(2-Naphthoylamido )-2-methyl-phenyl]-4-(3-pyridyl)-2-pyrimidine-amine, N-[5-(4-Chloro-benzoylamido )-2-methyl-phenyl]-4-(3-pyridyl)-2-pyrimidine-amine, N-[5-(2-Methoxy-benzoylamido )-2-methyl-phenyl]-4-(3-pyridyl)-2-pyrimidine-amine, N-(3-Trifluoromethoxy-phenyl)-4-(3-pyridyl)-2-pyrimidine-amine, N-(3-[1,1,2,2-tetrafluoro-ethoxy]-phenyl)-4-(3-pyridyl)-2-pyrimidine-amine, N-(3-Nitro-5-methyl-phenyl)-4-(3-pyridyl)-2-pyrimidine-amine, N-(3-Nitro-5-trifluoromethyl-phenyl)-4-(3-pyridyl)-2-pyrimidine-amine, N-(3-Nitro-phenyl)-4-(N-oxido-3-pyridyl)-2-pyrimidine-amine, N-(3-Benzoylamido-5-methyl-phenyl)-4-(N-oxido-3-pyridyl)-2-pyrimidine-amine and the pharmaceutically acceptable salts of such a compound having at least one salt-forming group.

20. A compound according to claim 1 of the formula I or a pharmaceutically acceptable salt of such a compound having at least one salt-forming group selected from N-[3-(1,1,2,2-tetrafluoroethoxy)phenyl]-4-(N-oxido-4-pyridyl)-2-pyrimidine-amine and N-[3-(1,1,2,2-tetrafluoroethoxy)phenyl]-4-(3-indolyl)-2-pyrimidine-amine and the pharmaceutically acceptable salts of such a compound having at least one salt-forming group.

21. A pharmaceutical composition for the treatment of tumours in warm-blooded animals including humans, comprising, in a dose effective against tumours, a compound of formula I according to claim 1, or a pharmaceutically acceptable salt of such a compound having at least one salt-forming group, together with a pharmaceutical carrier.

22. A method of treating warm-blooded animals including humans, which comprises administering to such a warm-blooded animal suffering from a tumoral disease a dose, effective against tumours, of a compound of formula I according to claim 1 or of a pharmaceutically acceptable salt of such a compound having at least one salt-forming group.

23. The compound according to claim 1 of the formula I, said compound being N-{5-[4-(4-Methyl-piperazino-methyl)-benzoylamido]-2-methyl-phenyl}-4-(3-pyridyl)-2-pyrimidine-amine or a pharmaceutically acceptable salt thereof.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 5,521,184 |
| (45) | ISSUED | : | May 28, 1996 |
| (75) | INVENTOR | : | Jürg Zimmerman |
| (73) | PATENT OWNER | : | NOVARTIS CORPORATION |
| (95) | PRODUCT | : | Gleevec® (imatinib mesylate) |

This is to certify that an application under 35 U.S.C. § 156 has been filed in the United States Patent and Trademark Office, requesting extension of the term of U.S. Patent No. 5,521,184 based upon the regulatory review of the product Gleevec® (imatinib mesylate) by the Food and Drug Administration. Since it appears that the requirements of the law have been met, this certificate extends the term of the patent for the period of

(94)  586 days from May 28, 2013, the original expiration date of the patent, subject to the payment of maintenance fees as provided by law, with all rights pertaining thereto as provided by 35 U.S.C. § 156(b).

I have caused the seal of the United States Patent and Trademark Office to be affixed this 7th day of January 200

JAMES E. ROGAN
Under Secretary of Commerce for Intellectual Property and Director of the United States Patent and Trademark Office